US008399075B2

(12) United States Patent
Beakler

(10) Patent No.: US 8,399,075 B2
(45) Date of Patent: Mar. 19, 2013

(54) SPALTED WOOD VENEERS AND SPALTED ENGINEERED WOOD FLOORING

(75) Inventor: Brian W. Beakler, York, PA (US)

(73) Assignee: Armstrong World Industries, Inc., Lancaster, PA (US)

( * ) Notice: Subject to any disclaimer, the term of this patent is extended or adjusted under 35 U.S.C. 154(b) by 0 days.

(21) Appl. No.: 13/611,028

(22) Filed: Sep. 12, 2012

(65) Prior Publication Data

US 2013/0004734 A1 Jan. 3, 2013

Related U.S. Application Data

(63) Continuation of application No. 11/901,361, filed on Sep. 17, 2007, now Pat. No. 8,287,971.

(60) Provisional application No. 60/918,605, filed on Mar. 16, 2007.

(51) Int. Cl.
*A41G 1/00* (2006.01)
*C12P 1/02* (2006.01)

(52) U.S. Cl. .......................................... 428/22; 435/171

(58) Field of Classification Search .................... 428/22; 435/171

See application file for complete search history.

(56) References Cited

PUBLICATIONS

Croan, "Evaluation of White-Rot Fungal Growth on Southern Yellow Pine Wood Chips Pretreated with Blue-Stain Fungi", The International Research Group on Wood Preservation Section 1 Biology 31st Annual Meeting, Kona, Hawaii, USA, pp. 1-9, May 2000.
A. Hilton, "Spalting, A Fungus Amongus", http://hiltonhandcraft.com/Articles/Spalting_a_Fungus_Amongus.asp, pp. 1-11, publication date for this web site article Mar. 12, 2007.
"White-rot Fungus", http://www.hawaii.edu/abrp/Technologies/fungus.html; pp. 1-3, publication date for this web site article Jul. 7, 2007.
"The Spalted Wood—One Man's Junk Another Man's Prize", http://www.dnr.state.oh.us/forestry/Industries/spalteedwood.htm, pp. 1-3, publication date for this web site article Mar. 8, 2007.
"Tips for creating Spalted Wood", http://www.woodweb.com/knowledge_base/Tips_for_creating_spalted_maple.html, printfriendly, pp. 1-2, Jan. 4, 2001.
"Intentional Spalting", http://www.woodweb.com/knowledge_base/International_Spalting.html, pp. 1-5, Jun. 23, 2005.
A. Lacer, "Spalted Wood", http://www.alanlacer.com/articles/spalting.html, pp. 1-5, publication date for this web site article Mar. 8, 2007.
"Producing Spalted Wood", USDA Forest Service, pp. 1-2, Mar. 2004, MO-1, Madison, WI.
"Blue Stain", USDA Forest Service, pp. 1-2, May 2002, Madison, WI.

*Primary Examiner* — Herbert J Lilling
(74) *Attorney, Agent, or Firm* — McNees Wallace & Nurick LLC

(57) ABSTRACT

A spalted wood product having a first ply cut from a wood and a second ply cut from the wood wherein the first ply and the second ply are spalted. The spalted first ply or spalted second ply is positioned on a base, where the base includes engineered wood, and the wood products include wood flooring.

20 Claims, No Drawings

SPALTED WOOD VENEERS AND SPALTED ENGINEERED WOOD FLOORING

CROSS REFERENCE TO RELATED APPLICATIONS

This application is a continuation of U.S. Utility application Ser. No. 11/901,361, filed on Sep. 17, 2007, and entitled "Spalted Wood Veneers, Spalted Engineered Wood Flooring and Method of Making", the disclosure of which is hereby incorporated by reference in its entirety.

FIELD OF THE INVENTION

The present invention is related to spalted wood veneers, spalted engineered wood flooring and the method of making the veneers and flooring.

BACKGROUND OF THE INVENTION

Spalted wood occurs naturally in forests in felled logs and trees which have been infected with spalt fungus (a combination of white rot and blue stain). The spalting makes the wood brittle and difficult to cut into lumber. Therefore, it has not been possible to cut the spalted wood into veneers.

According to the American National Standards Institute, a veneer is a thin sheet of wood, rotary cut, sliced, or sawed from a log, bolt or flitch. A veneer is referred to as a ply when assembled. The formation of spalted veneers would permit the manufacture of spalted engineered wood flooring having a spalted wood veneer decorative layer.

Naturally occurring spalted maple is traditionally used by artisans in lathe produced turnings, e.g. bowls and vases. While spalted solid wood floors have been made from lumber pieces cut from spalted logs, it has not been possible to cut the spalted logs into veneers for use in making engineered wood and engineered wood floors. If the decay progresses too far, the wood becomes punky, soft and spongy, stringy, ring-shaked, pitted or crumbly.

Spalting is a decay process in certain wood species that gives the wood a unique blotchy appearance having dark lines. White rot is a decay mechanism that yields thin distinctive lines with broad lighter colored areas in between the lines. White rot is caused by white rot decay fungi. The white rot attacks the cellulose and lignin giving the wood a whitish appearance and multicolored streaks of black, pink and gray. The white rot spores are typically airborne.

Blue stain does not contribute to the decay of the wood but does yield a yellow, orange, red, blue, black or brown coloration. It is caused by microscopic fungi that infect only the sapwood. The blue stain fungi are normally spread by spores that are carried into the wood by insects.

SUMMARY OF THE INVENTION

It is an object of the invention is to provide a spalted wood veneer, particularly a veneer that can be produced in a time frame to enable commercial production.

Another object of the invention is to provide engineered wood flooring, i.e. a multi-layered wood flooring product, having a spalted wood veneer decorative layer.

It is also an object of the invention to provide a method to manufacture a spalted wood veneer.

It is a further object of the present invention to provide a method to manufacture a spalted engineered wood flooring having a spalted wood veneer decorative layer.

DETAILED DESCRIPTION OF THE INVENTION

To form the spalted veneer, green (wet) wood is cut into veneers and then inoculated with the white rot (e.g. Phanerochaete chyrsosporium) and/or blue stain (e.g. Ceratocystis tenella) spores by coating the surfaces of the veneer with a solution containing the spores. Both of the major surfaces of the veneers can be efficiently coated with a roll coat system. Other means of inoculating the cut veneers is to spray the major surfaces of the veneers with a solution containing the white rot and/or blue stain spores. The environment of the impregnated veneers can be controlled to promote the rapid growth of the spalting and then stopped when the desired degree of spalting is achieved.

The invention is directed to any species of wood which can be cut into veneers and spalted. The wood species that can be used include maple, elm, beech, birch, buckeye, basswood, sycamore, apple, and the hickories. Red oak and white oak will also spalt. While walnut will spalt, it is dark in color and more difficult to observe.

White rot grows best at temperatures of from about 70° degree F. to about 90° degree F. and a wood moisture content of about 30% in an oxygen rich atmosphere. The best conditions for blue stain are temperatures between about 60° degree F. and about 150° degree F. and a wood moisture content of about 20% to about 30% in an oxygen rich atmosphere. For efficient growth of the white rot and blue stain spores, the wood veneer should have a moisture content of about 20% to about 40% during the spalting process.

Therefore, the inoculated veneers can be stacked into a chamber in which a preferred environment for spalting the veneer of about 50° degree F. to about 100°degree F. with about 50% RH to about 90% RH is maintained. No growth of the white rot is seen below about 50° degree F. A more preferred environment for processing the spalted veneers is a temperature of from about 70° degree F. to about 90° degree F. and about 70% RH to about 90% RH in an oxygen rich atmosphere.

Prior to loading the inoculated veneers into the chamber, the chamber could be sterilized with an ultraviolet light treatment to kill any other spores. The spalting process may take days, weeks or months, depending upon the type and condition of the wood and the environmental conditions. Samples are removed frequently and inspected to determine when the spalting process should be stopped. It is desired to allow the spalting to proceed to a point where the appearance is pleasing, but the structure of the veneer has not been overly weakened.

The spalting process can be halted by drying the veneers at a temperature of at least 130° degree F. After the spalting process has been stopped, the spalted veneers can be stabilized and/or stiffened by filling the spalted areas with waxes, oils, glues or impregnation chemicals, such as acrylics. The veneers are then glued to the engineered platform or base, and then tongue and groove edges, including locking tongue and groove edges, are typically machined into the engineered wood piece.

What is claimed is:

1. A spalted wood veneer product, comprising:

a first ply cut from a wood, and a second ply cut from the wood, wherein the first ply and the second ply are spalted.

2. The spalted wood veneer product of claim 1, wherein the spalted wood product comprises a base and one or both of the first ply and the second ply are positioned on the base.

3. The spalted wood veneer product of claim 2, wherein the base is engineered wood.

4. The spalted wood veneer product of claim 2, wherein one or both of the first ply and the second ply are glued to the base.

5. The spalted wood veneer product of claim 1, wherein the spalted wood product is wood flooring.

6. The spalted wood veneer product of claim 1, wherein the spalted wood product is resistant to further decay.

7. The spalted wood veneer product of claim 1, wherein the first ply and the second ply are rotary cut from the wood.

8. The spalted wood veneer product of claim 1, wherein the first ply and the second ply are sliced from the wood.

9. The spalted wood veneer product of claim 1, wherein first ply and the second ply are sawed from the wood.

10. The spalted wood veneer product of claim 1, wherein the spalted wood product is machined to include tongue and groove edges.

11. The spalted wood veneer product of claim 1, wherein the spalted wood product is machined to include locking tongue and groove edges.

12. The spalted wood veneer product of claim 1, wherein the wood comprises maple, elm, beech, birch, buckeye, basswood, sycamore, red oak, white oak, walnut, apple, or hickory.

13. The spalted wood veneer product of claim 1, wherein the first ply and the second ply are stabilized and stiffened by fillers.

14. The spalted wood veneer product of claim 13, wherein the fillers include waxes, glues, oils, impregnation chemicals, acrylics, or a combination thereof.

15. The spalted wood veneer product of claim 1, wherein the first ply and the second ply are spalted by one or both of *Phanerochaete chyrsosporium* and *Ceratocystis tenella*.

16. The spalted wood veneer product of claim 1, wherein the first ply and the second ply are spalted in an environment with between about 50% RH and about 90% RH.

17. The spalted wood veneer product of claim 1, wherein the first ply and the second ply are sterilized with ultraviolet light.

18. The spalted wood veneer product of claim 1, wherein the spalted wood comprises distinctive lines and multicolored streaks.

19. A spalted wood veneerproduct, comprising:

a first ply cut from a wood, and a second ply cut from the wood, wherein the first ply and the second ply were inoculated with spalting spore and spalting was deterred.

20. A spalted wood veneerproduct, comprising:

a first ply cut from a wood, and a second ply cut from the wood, wherein the first ply and the second ply are spalted and one or both of the first ply and the second ply are bonded to a base.

* * * * *